United States Patent
Richards et al.

(10) Patent No.: US 9,470,633 B2
(45) Date of Patent: Oct. 18, 2016

(54) METHOD, APPARATUS AND SYSTEM FOR TRANSMITTANCE MEASUREMENT

(71) Applicant: Google Inc., Mountain View, CA (US)

(72) Inventors: Evan M. Richards, Santa Clara, CA (US); Anurag Gupta, San Jose, CA (US)

(73) Assignee: Google Inc., Mountain View, CA (US)

( * ) Notice: Subject to any disclaimer, the term of this patent is extended or adjusted under 35 U.S.C. 154(b) by 64 days.

(21) Appl. No.: 14/181,083

(22) Filed: Feb. 14, 2014

(65) Prior Publication Data

US 2015/0233824 A1    Aug. 20, 2015

(51) Int. Cl.
*G01J 4/00* (2006.01)
*G01N 21/59* (2006.01)

(52) U.S. Cl.
CPC .................................. *G01N 21/59* (2013.01)

(58) Field of Classification Search
CPC ...... G01N 21/59; G01N 21/03; G01N 21/41; G02B 1/11; H01L 31/052
See application file for complete search history.

(56) References Cited

U.S. PATENT DOCUMENTS

| | | | |
|---|---|---|---|
| 3,591,287 A | 7/1971 | Hannis | |
| 3,951,609 A | 4/1976 | Palenscar | |
| 4,123,173 A | 10/1978 | Bullock et al. | |
| 4,277,177 A | 7/1981 | Larsen et al. | |
| 4,747,687 A | 5/1988 | Hoppe et al. | |
| 5,228,462 A | 7/1993 | Osmalov et al. | |
| 5,314,825 A | 5/1994 | Weyrauch et al. | |
| 5,546,179 A | 8/1996 | Cheng | |
| 5,892,577 A * | 4/1999 | Gordon | ............... 356/73 |
| 6,078,443 A | 6/2000 | Yu | |
| 6,239,871 B1 | 5/2001 | Gilby | |
| 6,483,590 B1 | 11/2002 | Davis | |
| 6,646,678 B1 | 11/2003 | Kobayashi | |
| 6,927,852 B2 | 8/2005 | Reel | |
| 7,177,023 B2 | 2/2007 | Reel et al. | |
| 7,538,878 B2 | 5/2009 | Jung et al. | |
| 8,054,453 B2 | 11/2011 | Harrison | |
| 8,299,416 B2 | 10/2012 | Arbore et al. | |
| 8,591,836 B2 | 11/2013 | Boege et al. | |
| 2005/0037484 A1 | 2/2005 | Staimer et al. | |
| 2011/0188030 A1* | 8/2011 | Verschuren et al. | ........ 356/128 |
| 2012/0088486 A1 | 4/2012 | Messerchmidt | |
| 2013/0247959 A1* | 9/2013 | Kwon et al. | ............ 136/246 |

OTHER PUBLICATIONS

U.S. Appl. No. 14/015,569, filed Aug. 30, 2013, U.S. Office Action mailed Oct. 21, 2014 (22 pages).
U.S. Appl. No. 14/015,569, filed Aug. 30, 2013, U.S. Notice of Allowance mailed Jan. 8, 2015 (18 pages).
"U.S. Appl. No. 14/015,569, Entitled "Instrument for Reflectivity Measurement", filed Aug. 30, 2013", (Aug. 30, 2013), Whole Document.

* cited by examiner

*Primary Examiner* — Tarifur Chowdhury
*Assistant Examiner* — Jamil Ahmed
(74) *Attorney, Agent, or Firm* — Blakely Sokoloff Taylor & Zafman LLP (57) ABSTRACT

An apparatus for testing transmittance includes a sample unit to position a material under test. The material under test is disposed between respective flat surfaces of a first mount and a second mount, which are positioned in the sample unit for a test round. The sample unit defines a first volume and a second volume, wherein arc shapes, variously formed by respective surfaces of the first and second volume, conform to an imaginary circle. During the test round, a rotation unit successively changes an angular position of the MUT relative to a light source. A light detector receives light from the light source which has been transmitted through the first volume, the MUT and the second volume. Based on the received light, a transmittance signature of the MUT is determined for a range of incidence angles.

20 Claims, 6 Drawing Sheets

FIG. 6B

METHOD, APPARATUS AND SYSTEM FOR TRANSMITTANCE MEASUREMENT

BACKGROUND

1. Technical Field

This disclosure relates generally to instruments for measuring optical properties of materials.

2. Background Art

The evaluation of a material's optical characteristics can include testing some or all of transmittance, reflectance and absorbance for the material under various conditions. Transmittance is a measurement of the fraction of incident light (electromagnetic power) that passes through a material. Transmittance is a positive real number and is equal to a ratio of the power of light which is transmitted through a sample material to the power of light which is originally incident upon that sample material. The transmittance of a material layer can vary with a variety of factors such as light's angle of incidence, its wavelength, and its polarization. Thus, to fully characterize the transmittance of a material layer for a specific wavelength, transmittance measurements should be taken at a variety of different incident angles. Fully and accurately characterizing the transmittance of a material layer can be a time consuming process.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of a system, apparatus, and method of operation for measuring transmittance signature as a function of incident angle in an automated manner are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
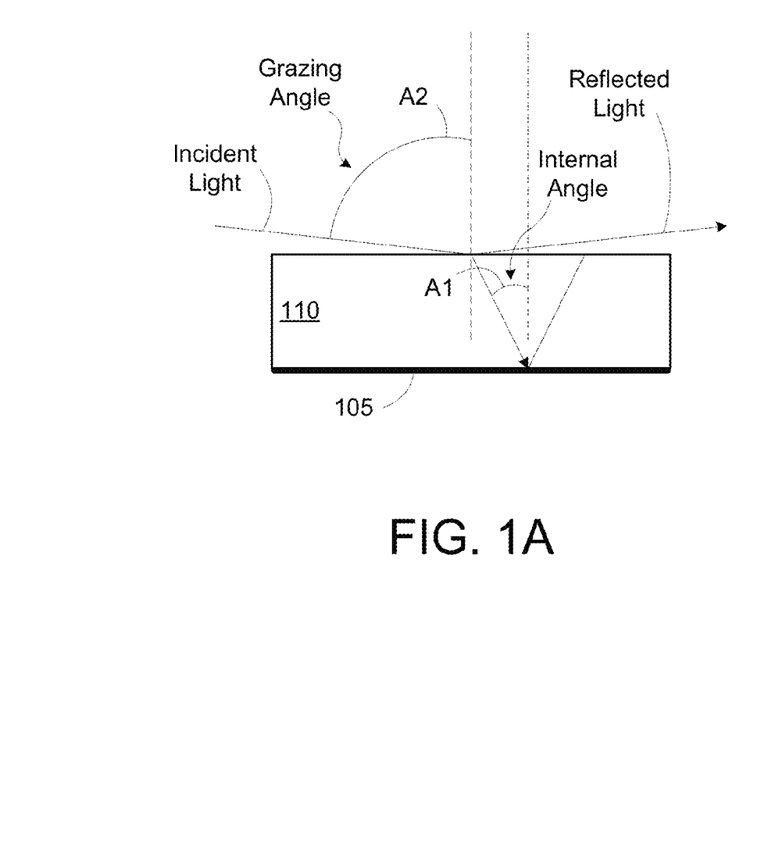
FIGS. 1A, 1B illustrate issues associated with measuring the transmittance of a material deposited below a surface.

It can be relatively straightforward to measure the transmittance of a material layer on a front surface of a planar substrate for all possible angles of incidence. However, this is not the cases when the material layer is disposed below or embedded within a substrate having an index of refraction greater than air. FIG. 1A illustrates such a scenario where a material layer 105 is disposed below a substrate 110 having an index of refraction greater than air. As illustrated for substrate 110 in air, Snell's Law does not allow the internal angle A1 to exceed the critical angle given by $\sin^{-1}(1/n)$, where n is the index of refraction for the material of substrate 110. Thus, even though the external angle of incidence A2 at the top surface of substrate 110 is a grazing angle or near 90 degrees from normal, the internal angle of incidence A1 at the buried material layer 105 is substantially less and limited by Snell's Law. This problem would also apply to various cases where substrate 110 is immersed in a material having an index of refraction less than n.

Figure 1B:
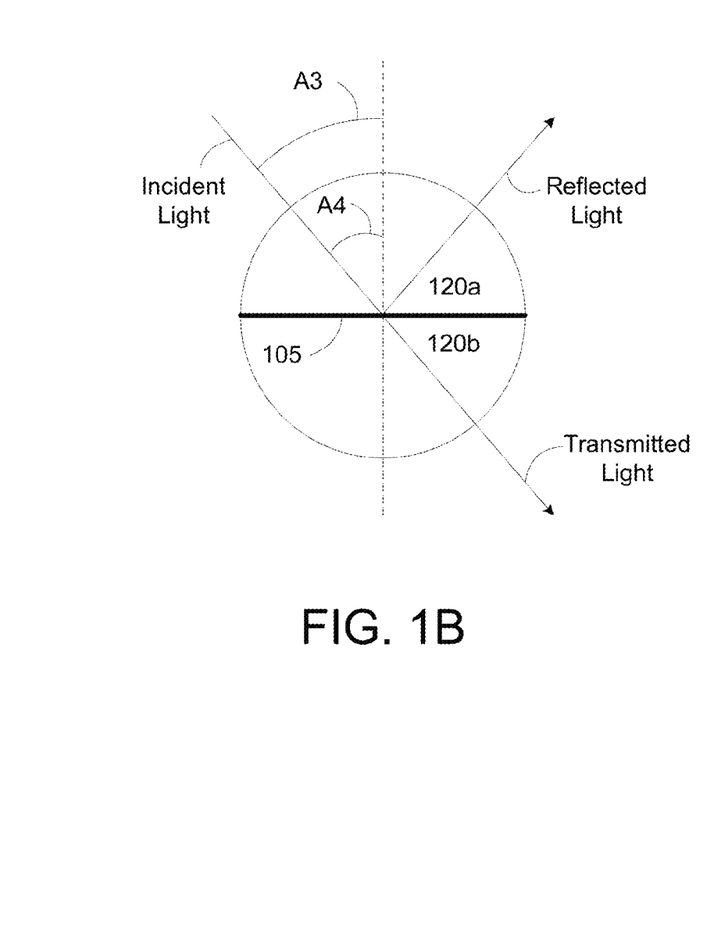

Referring to FIG. 1B, the limitations imposed by Snell's Law can be overcome by disposing material layer 105 between two mounts 120a, 120b which positions relative to one another result in respective cross-sections of mounts 120a, 120b conforming to the same imaginary circular shape. One or both of mounts 120a, 120b may be made of the same material as substrate 110 having an index of refraction greater than that of air. However, if the angle of incidence A3 at the top surface of mount 120a is constrained to always be normal to the surface of mount 120a, then the angle of incidence A4 of the light at the surface of material layer 105 will match the angle of incidence A3 and can be tested for all angles 0 through 90 degrees. Embodiments describe herein leverage this technique in an automated system for measuring transmittance signatures as a function of incident angle.

Figure 2A:
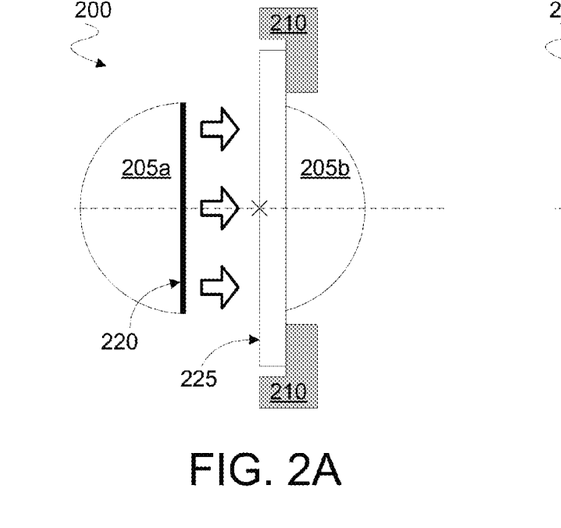
FIGS. 2A-2C illustrate different views and perspectives of a sample unit for measuring transmittance according to an embodiment.
Figure 2B:
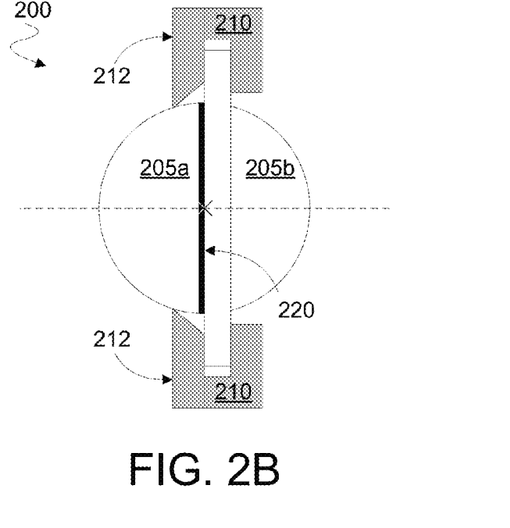
Figure 2C:
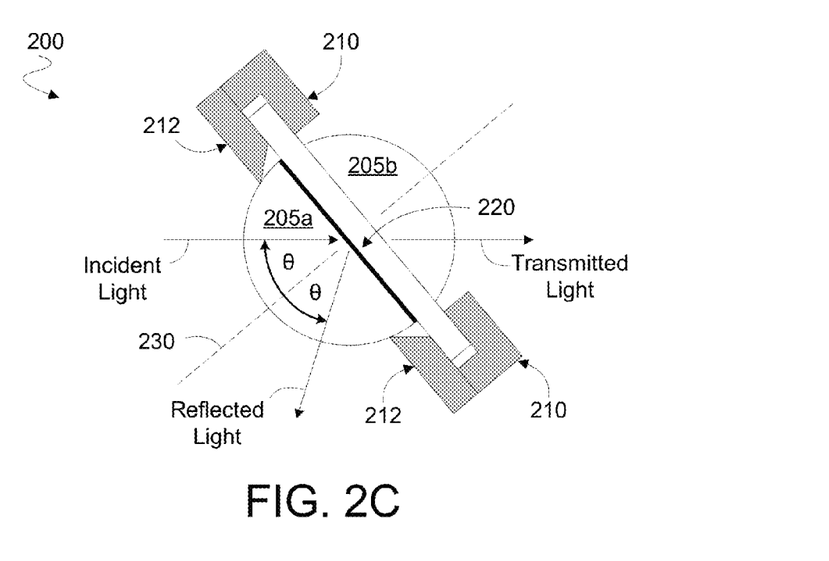

FIGS. 2A-2C illustrate different cross-sectional views of a sample unit 200 according to an embodiment for measuring transmittance of a material as a function of incidence angle. FIG. 2A is an assembly view of sample unit 200, FIG. 2B is a view of the assembled sample unit 200, and FIG. 2C is a view of sample unit 200 during a test round comprising a plurality of tests to variously measure transmittance of a material under test (MUT) 220.

In the illustrated embodiment, sample unit 200 defines at least in part a first volume 205a and a second volume 205b—e.g. where sample unit 200 includes sidewalls which variously define respective curved surfaces of volumes 205a, 205b. Such curved surfaces may form respective arc shapes which each conform to, or may be aligned to conform to, the same imaginary circular shape. For example, one or both of volumes 205a, 205b may be hemispherical or hemicylindrical.

By way of illustration and not limitation, volume 205a may be defined at least in part by a structure (referred to herein as a mount) comprising a light-transmissive solid material—e.g. glass, plastic, etc.—having the shape of volume 205a. Volume 205b may be similarly defined by another mount which comprises the same (or a different) light-transmissive material having the shape of volume 205b. In an embodiment, sample unit 200 includes mounts which provide mechanical support for MUT 220 during a test round. For example, MUT 220 may be a thin film coating which is deposited on a flat surface of one mount and then bonded to the flat surface of another mount—e.g. using an optically-transmissive adhesive.

In another embodiment, volume 205a (and/or volume 205b) may be formed by a chamber including one or more interior sidewalls which define the curved surface of volume 205a (and/or the curved surface of 205b). During a test round, such a chamber may have disposed therein a mount on which is disposed MUT 220, another mount adjacent to MUT 220 and/or a light transmissive liquid. Such a liquid may surround or otherwise adjoin one or both such mounts—e.g. where the liquid is index-matched with an index of refraction of one or both such mounts.

Sample unit 200 may further comprise a frame to securely position MUT 220 within in and/or between volumes 205a, 205b. By way of illustration and not limitation, such a frame may include a retaining ring 210 to receive and support a lip 225 other such structure formed in or extending from a mount positioned in volume 205b. The frame may further include or couple to an alignment plate 212 to couple with retaining ring 210 to provide alignment of volumes 205a, 205b relative to one another. As shown in FIG. 2C, light beams may be variously aimed during a test round along different angles θ—relative to a line normal to flat surface of MUT 220—at a center of the circle to which volumes 205a, 205b variously conform.

Due to the curved surface of volume 205a (and/or the curved surface of volume 205b), a light transmissive material which defines or otherwise conforms to that curved surface will not cause a variable amount of reflection where light enters that light transmissive material for targeting MUT 220. Consequently, measurement of optical characteristics of MUT 220 may take place for a wide range of incidence angles—e.g. depending on the specific hardware configuration, up to 90° as measured from a line 230 normal to the target surface of MUT 220.

Figure 3A:
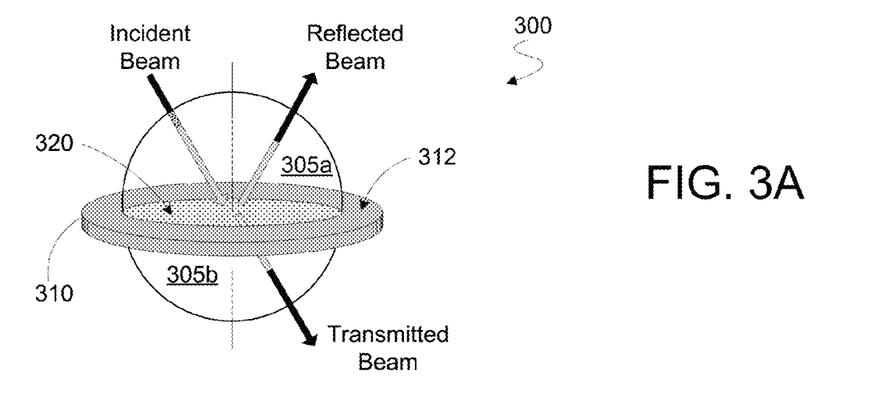
FIGS. 3A-3C illustrate different views and perspectives of a sample unit including hemispherical mounts according to an embodiment.
Figure 3B:
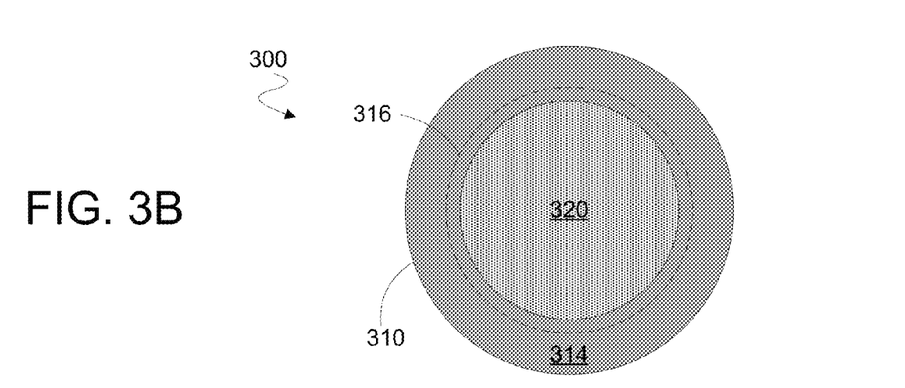
Figure 3C:
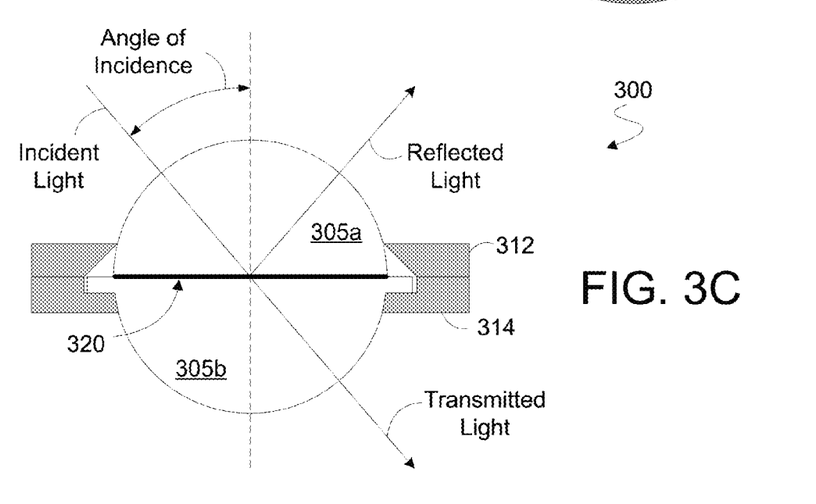

FIGS. 3A-3C illustrate different views and perspectives of a sample unit 300 for measuring the transmittance of a material layer as a function of angle, in accordance with an embodiment. Sample unit 300 may include some or all of the features of sample unit 200, for example. FIG. 3A is a perspective view of sample unit 300, FIG. 3B is a top view of sample unit 300, and FIG. 3C is a cross-sectional view of sample unit 300.

The illustrated embodiment of sample unit 300 includes a first mount 305a which defines at least in part a first volume—in this example, a hemispherical volume—which is disposed over a material layer 320 to be tested. Alternatively or in addition, material layer 320 may be disposed over a second mount 305b of sample unit 300 which defines at least in part a second (e.g. hemispherical) volume. Material layer 320 may be painted, coated, adhered, sputtered or otherwise deposited on one or each of the respective flat surfaces of mounts 305a, 305b.

In the illustrated embodiment, mounts 305a, 305b may include or couple to a frame 310 for securing a position of mounts 305a, 305b relative to one another. Although certain embodiments are not limited in this regard, frame 310 may extend to create a circular flange 316, which may be used for mounting (or otherwise securing) sample unit 300 into an automated system for measuring a transmittance signature of material layer 320. Such mounting may be performed using any of a variety of mechanisms including mechanical clasps, temporary glue, pressure fit, threaded attachment, or otherwise. By way of illustration and not limitation, frame 310 may include a retaining ring 314 having formed therein a recess to receive and support a lip, tab, rim or other such structure formed in or extending from mount 305b. An alignment plate 312 of frame 310 may be coupled with retaining ring 314 to align mount 305a relative to mount 305b—e.g. for respective cross-sections of mounts 305a, 305b to conform to the same imaginary circular shape.

Such positioning of mounts 305a, 305b may provide that, for beams variously directed along different angles of incidence relative to a target surface of material layer 320, the beams are each normal to the curved side of mount 305a at a point where the beam enters mount 305a. Such positioning may further provide that, for beams variously transmitted along different angles away from the target surface of material layer 320, the beams are each normal to the curved side of mount 305b at a point where the beam exits mount 305b.

One or each of mounts 305a, 305b need not be a complete hemisphere, but rather may be implemented with less than a full portion of a hemisphere. However, in such an embodiment, the respective planar surfaces onto which material layer 320 is disposed may be positioned such that at least one point of material layer 320 is located at a position where all rays normal to a curved side of a cross-section of mount 305a (or of a cross-section of mount 305b) intersect.

A portion of mounts 305a, 305b may be formed of a single contiguous block of material with frame 310 or, alternatively, frame 310 may be bonded or otherwise coupled to such a portion of mounts 305a, 305b. In an embodiment, one or each of mounts 305a, 305b is fabricated of plastic (e.g., PMMA, Zeonex™ E48R, etc.), glass, or other optically transmissive materials.

Figure 4:
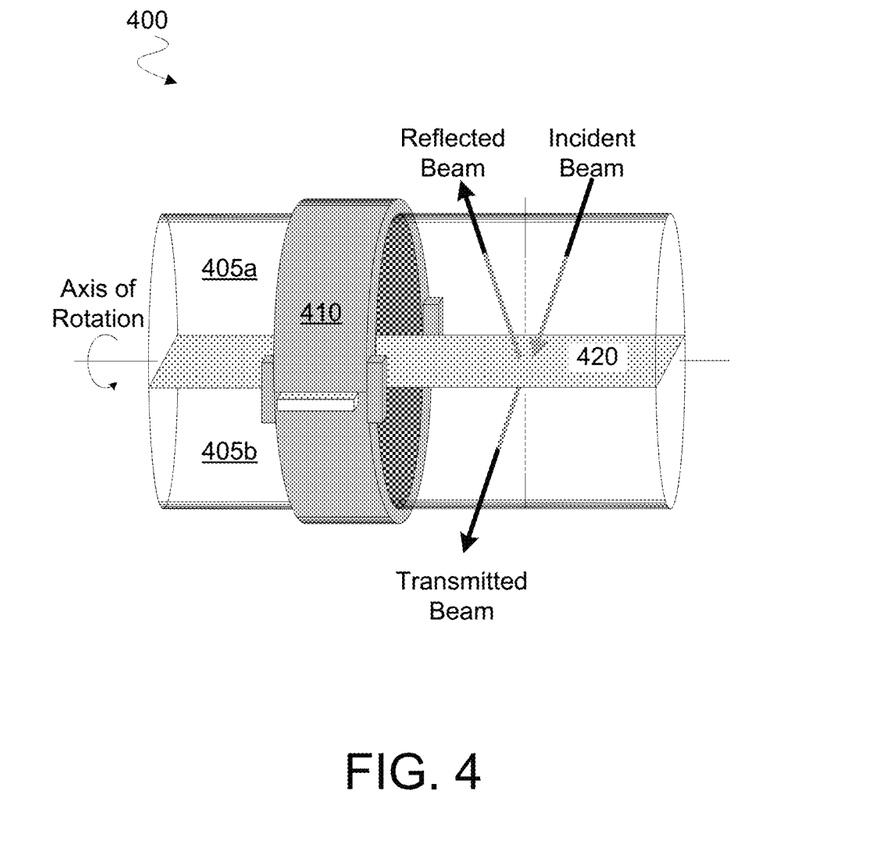
FIG. 4 is a perspective view of a sample unit including hemicylindrical mounts according to an embodiment.

FIG. 4 is a perspective view of a sample unit 400 according to according to an embodiment for positioning a MUT during testing of the MUT's optical characteristics (e.g. transmittance, reflectance and/or the like). Sample unit 400 may include some or all of the features of sample unit 200, for example. As contrasted with the generally spherical volume for transmitting light in sample unit 300, sample unit 400 defines a generally cylindrical volume for light transmission during a test round.

By way of illustration and not limitation, the embodiment of sample unit 400 includes mounts 405a, 405b, where a material layer 420 is disposed between respective flat surfaces of mounts 405a, 405b for transmittance (or other) testing of material layer 420. Material layer 420 may be adhered or otherwise bonded to at least one such flat surface of mounts 405a, 405b, for example.

Each of mounts 405a, 405b define at least in part a respective hemicylindrical volume. For example, mounts 405a, 405b may each comprise a respective light-transmissive solid having a hemicylindrical shape. In the illustrated embodiment, mounts 405a, 405b couple to a frame 410 for securing a position of mounts 405a, 405b relative to one another. Frame 410 may provide functionality corresponding to that of frame 310, for example. Although certain embodiments are not limited in this regard, frame 410 may include portions which are hingedly, flexibly or otherwise movably coupled to one another to allow for opening of frame 410 for receiving of one or both of mounts 405a, 405b. Such portions may be subsequently bolted, locked, clasped, bonded or otherwise fixed to secure positioning of mounts 405a, 405b.

For example, respective curved surfaces of mounts 405a, 405b may each form a corresponding arc shape. Frame 410 may include a flange, a bracket and/or other hardware operable to mechanically align mounts 405a, 405b with respect to one another so that such arc shapes are located to conform to the same imaginary circle. Such alignment may provide that, for beams variously directed along different angles of incidence relative to a target surface of material layer 420, each of the beams is normal to the curved side of mount 405a at a point where the beam enters mount 405a. Such positioning may further provide that, for beams variously transmitted along different angles away from the target surface of material layer 420, the beams are each normal to the curved side of mount 405b at a point where the beam exits mount 405b. The various angles of light transmission may be achieved by successively changing an angular position of material layer 420 relative to a light source (not shown) which emits the incident beams—e.g. by rotation of sample unit 400 on the axis of rotation shown.

Figure 5:
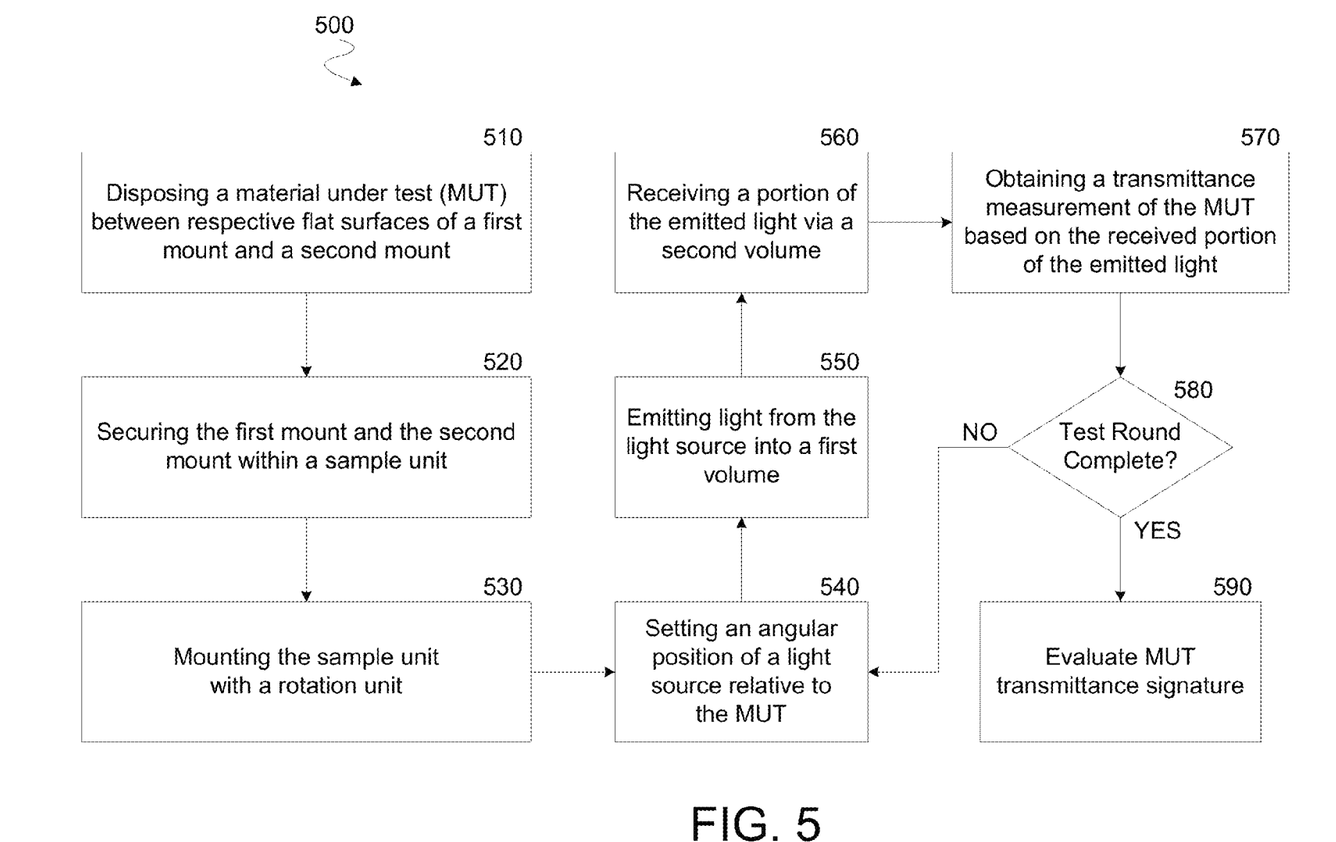
FIG. 5 is a flow chart illustrating a process for measuring a transmittance signature for a material under test

FIG. 5 is a flow chart illustrating a method 500 for measuring a transmittance signature for a material under test, in accordance with an embodiment. Method 500 describes the use and operation of an illustrative automated system 600 shown in FIG. 6A. The order in which some or all of the process blocks appear in method 500 should not be deemed limiting. Rather, one of ordinary skill in the art having the benefit of the present disclosure will understand that some of the process blocks may be executed in a variety of orders not illustrated, or even in parallel. One of ordinary skill in the art having the benefit of the present disclosure will also understand that method 500 may include one or more additional operations (not shown) to provide any of various other features discussed herein.

Figure 6A:
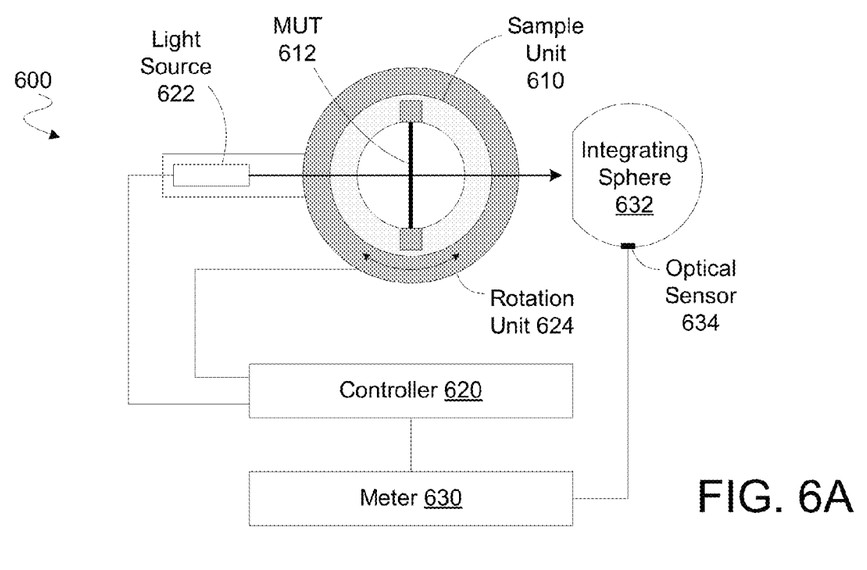
FIGS. 6A, 6B are perspective views each of a respective apparatus for measuring optical characteristics of a material according to a corresponding embodiment.

In an embodiment, method 500 includes operations to position a MUT in a sample unit which defines at least in part a first volume and a second volume. Examples of such a sample unit and MUT according to one embodiment are represented by sample unit 610 and MUT 612 of system 600. The positioning of MUT include, at 510, disposing MUT 612 between respective flat surfaces of a first mount and a second mount. For example, MUT 612 may comprise a thin film or other coating which is disposed on a flat surface of one of mounts 305a, 305b (or a flat surface of one of mounts 405a, 405b, in another embodiment) to provide rigid support for the coating during a test round.

Method 500 may, at 520, secure the first mount and the second mount within sample unit 610. A first surface of the first volume may form a first arc shape and a second surface of the second volume may form a second arc shape. Prior to or during the securing at 520, the first arc shape and the second arc shape may be positioned to conform to an imaginary circle. For example, the sample unit 610 may comprise a frame which is operable to align the respective curved surfaces of the first and second mounts with one another and/or to mechanically or chemically secure that alignment. In another embodiment, MUT 612 may be disposed between mounts which are not necessarily hemispherical or hemicylindrical. For example, sample unit 610 may comprise a housing which defines a chamber including the first volume and the second volume.

Method 500 may further comprise, at 530, mounting the sample unit with a rotation unit. For example, sample unit 610 may be mounted to a rotation unit 624 using any of a variety of mechanisms including mechanical clasps, temporary glue, pressure fit, threaded attachment, or otherwise. The rotation unit 624 may include or operate with any of a variety of motors, gears, belts or other such mechanical means for providing rotation of sample unit 610 relative to some other structure of system 600. For example, operation of rotation unit 624 may provide for changing a relative angular position of MUT 612 with respect to a light source which is to provide light for a test round. Alternatively or in addition, such operation may provide for changing a relative angular position of MUT 612 with respect to a light detector which is to receive light during the test round.

With the sample unit mounted at 530, method 500 may perform a test round including a plurality of tests each corresponding to a different respective angular position of light relative to the MUT. During the test round, the first volume may include a first light transmissive material and the second volume may include a second light transmissive material (which, for example is the same as the first light transmissive material). Such material or materials may be provided by a mount or mount—and, in some embodiments, an index matched liquid adjoining such mount or mounts—to facilitate consistency of an index of refraction between the first arc shape and the MUT and/or another consistency of an index of refraction between the second arc shape and the MUT.

In one illustrative embodiment, a test round includes, at 540, setting, with the rotation carriage, a current angular position of the light source relative to the MUT. For example, system 600 may include a controller 620 comprising any of a variety of hardware logic and/or executing software logic, where controller 620 is to provide to rotation unit 624 control signals to adjust an orientation of sample unit 610 relative to a light source 622. Light source 622 may be moved around a stationary sample unit 610, or vice versa. In an embodiment, a light detector such as the illustrative integrating sphere 632 is aligned with an output of light source 622—e.g. at least for tests of the test round which are to measure transmittance of MUT 612.

Light Source 622 may be a collimated, or nearly collimated, source for light to be directed at a target area of MUT 612. In an embodiment, light source 622 includes a monochromatic (e,g., laser) or broadband (such as tungsten, xenon, LED) source. As discussed herein, light source 622 may also include or operate with a polarization control mechanism (not shown) during the test round. Polarization control may be provided with any of a variety of devices that may produce various output light polarization states for a given input light polarization state. Such devices include, but are not limited to, linear polarizers, wave plates, crystals and/or the like. Polarization control may be optional, and is not limiting on certain embodiments. In an embodiment, light source 622 further includes or operates with a power stabilization feedback loop to control an output power level of light.

With the angular position set at 540, method 500 may, at 550, emit light from the light source into the first volume. The emission of light at 540 may be controlled by controller 620 or other control logic of system 600—e.g. where controller 620 variously sets one or more of a timing, wavelength and/or polarity of light to be emitted at 540. The light emitted at 550 may be directed toward a center of an imaginary circle to which the first arc shape and the second arc shape conform. In an embodiment, a point of MUT 612 is located at that center, which may also be located on an axis of rotation provided by rotation unit 624.

With a light detector—such as the illustrative integrating sphere 632 of system 600—method 500 may, at 560, receive via the second surface a portion of the light emitted at 540. The light received at 560 may be measured using one or more photodiodes, a spectrometer and/or any of various photodetection mechanisms. Although certain embodiments are not limited in this regard, one or more collimating lens and/or any of a variety of other such optics may additionally or alternatively be adapted to capture, direct and/or otherwise receive light at 560.

Based on the received portion of the emitted light, method 500 may, at 570, obtain a transmittance measurement of the MUT. For example, integrating sphere 632 may include or couple to an optical sensor 634 which is to output a signal indicating a level of power for light received by the integrating sphere at 560. The signal may be provided by optical sensor 634 to hardware and/or software logic—represented by the illustrative meter 630 of system 600—which is to process such signals to generate a measurement of received power.

In an embodiment, measurement operations of meter 630 are to take into account an indication of power for light output by light source 622 and/or one or more corrections factors. For example, meter 630 may receive—e.g. from controller 620—information describing a power level for incident light directed at MUT 612. Alternatively or in addition, meter 630 may determine an adjusted power measurement which accounts for absorption by sample unit 610 and/or for Fresnel losses for light passing through one or both of the respective curved surfaces of the first volume and the second volume. Such sample unit absorption and/or Fresnel losses may be determined either by calculation or by running a reference scan—e.g. where power loss is evaluated for light which is directed through sample unit 610 while the MUT 612 is not positioned in the sample unit 610.

After a given test of the test round, a determination may be made, at 580, as to whether the test round has completed. Where the test round is not yet completed, method 500 may proceed to a next test of the test round—e.g. by returning to operation 540 to set another angular position corresponding to the next test. Where the determining at 580 identifies that the test round is completed, method 500 may perform, at 590, evaluating a transmittance signature of the MUT. For example, meter 630 may calculate or otherwise identify a relationship of transmittance values (each representing a ratio of power for light transmitted through MUT 612 to power for corresponding light directed at a MUT 612) as a function of light wavelength, light polarization, light power and/or the like.

In an embodiment, method 500 includes additional operations (not shown) to iterate through a plurality of test rounds which, for example, each include respective operations corresponding functionally to operations 540 through 570. For example, method 500 may iterate through a plurality of test rounds which each correspond to a different respective polarization for light to be used during that test round. During each such test round, the MUT may be evaluated with light having a polarization state corresponding to that test round. Alternatively or in addition, method 500 may iterate through test rounds which, similarly, each correspond to a different respective frequency, a different respective power level and/or any of various other light characteristics.

Figure 6B:
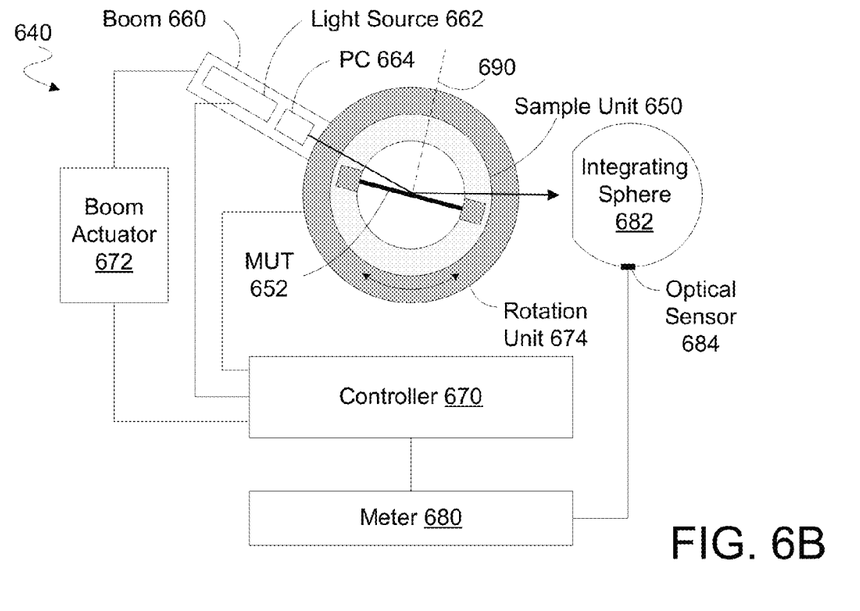

Alternatively or in addition, a system having some or all of the features of system 600 may determine various reflectance values each representing a ratio of power for light reflected off of a surface of a MUT to power for corresponding light directed at that surface. Such reflectance (also known as reflectivity) values may be similarly determined, for example, for a range of light wavelength values, a range of light polarization values and/or the like. FIG. 6B illustrates an example of one such system 640 according to an embodiment. In the illustrative system 640, a sample unit 650 includes a MUT 652 to be tested for one or both of transmittance and reflectance. Sample unit 650 and MUT 652 correspond, respectively, to sample unit 610 and MUT 612. Testing of MUT 652 may be performed with a rotation unit 674, controller 670, light source 662, integrating sphere 682 and meter 680 which, for example, correspond functionally to rotation unit 624, controller 620, light source 622, integrating sphere 632 and meter 630.

To provide for measurement of both transmittance and reflectance, system 640 may comprise a boom 660 which includes or couples to light source 622. Boom 660 may be movable with a boom actuator 672 comprising (for example) electric, hydraulic, pneumatic and/or any of various other types of mechanisms configured to facilitate rotation of light source 662 relative to MUT 652 and integrating sphere 682. During a test round, boom actuator 672 may operate in response to controller 670, for example, to sequentially position boom 660 for various angles of incidence of light to be directed at MUT 652. Although certain embodiments are not limited in this regard, a polarization control mechanism 664 may also be included in or coupled to light source 662 for measuring transmittance and/or reflectance across a range of light polarization values.

For tests to measure transmittance of MUT 652, rotation unit 674 and boom actuator 672 may be operated to align an input aperture of integrating sphere 682 with an output of light source 662. By contrast, tests to measure reflectance of MUT 652 may require operation of rotation unit 674 and boom actuator 672 to variously align light source 662 and the input aperture of integrating sphere 682 along opposite respective angles, as measured from a line 690 normal to the target area of MUT 652. In an embodiment, integrating sphere 682 includes or couples to an optical sensor 684 which is to output a signal indicating to meter 680 a level of power for light received by the integrating sphere 682.

In some embodiments, system 640 includes an additional light detector (not shown), such as another integrating sphere, which is aligned to receive light transmitted through MUT 652 concurrent with integrating sphere 682 receiving light reflected from a surface of MUT 652. By measuring a transmittance value T for light transmitted through MUT 652 and reflectance value R for light reflected from MUT 652, an absorption value A for light absorbed by MUT 652 may be calculated as:

$$A = 1 - T - R \qquad (1)$$

The processes explained above may be described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for testing transmittance, the apparatus comprising:
    a sample unit to define at least in part a first volume on a first side of a flat plane and a second volume on a second side of the flat plane, wherein a first curved surface of the first volume forms a first arc shape and a second curved surface of the second volume forms a second arc shape, together the first arc shape and the second arc shape to conform to a circle, the sample unit further to position a material under test (MUT) between a first mount disposed at least in part on the first side and a second mount disposed at least in part on the second side, including the sample unit to position the MUT between the first volume and the second volume;
    a light source coupled to move to different angular positions relative to the MUT during a test round performed by the apparatus, wherein the first volume includes a first light transmissive material and the second volume includes a second light transmissive material during the test round and the test round includes a first plurality of tests each corresponding to one of the different angular positions;
    a first light detector;
    metering logic, wherein for each of the first plurality of tests:
        the light source emits light into the first volume via the first curved surface; and
        the first light detector receives a first portion of the emitted light via the second curved surface, the first portion other than any portion of the emitted light that is reflected by the MUT, the metering logic including circuitry to generate, based on the received first portion of the emitted light, a signal representing a measurement of light transmittance through the MUT; and
    a rotation unit to mount the sample unit, wherein during the test round the rotation unit successively changes an angular position of the light source relative to the MUT.

2. The apparatus of claim 1, wherein the first volume is hemicylindrical.

3. The apparatus of claim 1, wherein the first volume is hemispherical.

4. The apparatus of claim 1, wherein a curved surface of the first mount includes the first arc shape.

5. The apparatus of claim 1, wherein the apparatus to perform a plurality of test rounds including the first test round, the plurality of test rounds each corresponding to a different respective polarization state of light to be provided for evaluating the MUT.

6. The apparatus of claim 1, wherein the circuitry to generate the signal representing the measurement further based on a value representing absorption of light by the sample unit.

7. The apparatus of claim 6, wherein the value representing absorption of light is determined based on a reference scan.

8. The apparatus of claim 1, wherein the circuitry to generate the signal representing the measurement further based on a value representing Fresnel losses.

9. The apparatus of claim 1, further comprising a second light detector, wherein for each of the first plurality of tests:
    the second light detector to receive via the first curved surface a second portion of the emitted light for the test; and
    the metering logic further to generate, based on the received second portion of the emitted light, a signal representing a reflectance measurement of the MUT.

10. The apparatus of claim 1, the test round further comprising a second plurality of tests each corresponding to a different respective angular position of the light source relative to the MUT, wherein for each of the second plurality of tests:
    the light source to emit light into one of the first volume and the second volume;
    the first light detector to receive a second portion of the emitted light via the one of the first volume and the second volume; and
    the metering logic to generate, based on the received second portion of the emitted light, a signal representing a reflectance measurement of the MUT.

11. A method comprising:
    positioning a material under test (MUT) in a sample unit which defines at least in part a first volume on a first side of a flat plane and a second volume on a second side of the flat plane, wherein a first curved surface of the first volume forms a first arc shape and a second curved surface of the second volume forms a second arc shape, the positioning the MUT including:
        disposing the MUT between a first mount disposed at least in part on the first side and a second mount disposed at least in part on the second side, including positioning the MUT between the first volume and the second volume; and
        securing the first mount and the second mount within the sample unit, wherein the first arc shape and the second arc shape are positioned to conform to an imaginary circle;
    mounting the sample unit with a rotation unit; and
    performing a test round during which the first volume includes a first light transmissive material and the second volume includes a second light transmissive material, the test round including a first plurality of tests each corresponding to a different respective angular position of a light source relative to the MUT, the test round including:
        for each of the first plurality of tests:
            emitting light from the light source into the first volume via the first curved surface;
            with a first light detector, receiving a first portion of the emitted light via the second curved surface, the first portion other than any portion of the emitted light that is reflected by the MUT; and
            obtaining a measurement of light transmittance through the MUT based on the received first portion of the emitted light; and
        successively changing an angular position of the light source relative to the MUT.

12. The method of claim 11, wherein the first volume is a hemicylindrical volume.

13. The method of claim 11, wherein the first volume is a hemispherical.

14. The method of claim 11, wherein a curved surface of the first mount includes the first arc shape.

15. The method of claim 11, wherein the first test round is one of a plurality of test rounds each corresponding to a different respective polarization state of light to be provided for evaluating the MUT, the method further comprising performing the others of the plurality of test rounds.

16. The method of claim 11, wherein the measurement of light transmittance through the MUT is obtained based on a value representing absorption of light by the sample unit.

17. The method of claim 16, wherein the value representing absorption of light is determined based on a reference scan.

18. The method of claim 11, wherein the measurement of light transmittance through the MUT is obtained based on a value representing Fresnel losses.

19. The method of claim 11, the test round further including, for each of the first plurality of tests:

with a second light detector, receiving via the first curved surface a second portion of the emitted light for the test; and obtaining a reflectance measurement of the MUT based on the received second portion of the emitted light.

20. The method of claim 11, the test round further comprising a second plurality of tests each corresponding to a different respective angular position of the light source relative to the MUT, the second plurality of tests each including:

emitting light into one of the first volume and the second volume;

with the first light detector, receiving a second portion of the emitted light via the one of the first volume and the second volume; and obtaining a reflectance measurement of the MUT based on the received second portion of the emitted light.

* * * * *